US012336935B2

(12) United States Patent
Lavi et al.

(10) Patent No.: US 12,336,935 B2
(45) Date of Patent: Jun. 24, 2025

(54) APPARATUS FOR TISSUE REMOVAL

(71) Applicants: SANOCULIS LTD., Kiryat Ono (IL); TEL HASHOMER MEDICAL RESEARCH INFRASTRUCTURE AND SERVICES LTD., Tel Hashomer (IL)

(72) Inventors: Gilad Lavi, Rishon Le'zion (IL); Yoseph Glovinsky, Petah Tiqwa (IL); Vadim Shmukler, Rishon Le'Zion (IL); Nir Israeli, Kiryat Ono (IL)

(73) Assignees: SANOCULIS LTD, Kiryat Ono (IL); TEL HASHOMER MEDICAL RESEARCH INFRASTRUCTURE AND SERVICES LTD., Tel Hashomer (IL)

( * ) Notice: Subject to any disclaimer, the term of this patent is extended or adjusted under 35 U.S.C. 154(b) by 269 days.

(21) Appl. No.: 17/964,299

(22) Filed: Oct. 12, 2022

(65) Prior Publication Data
US 2023/0146263 A1    May 11, 2023

Related U.S. Application Data

(63) Continuation of application No. 16/337,288, filed as application No. PCT/IL2016/051063 on Sep. 27, 2016, now Pat. No. 11,471,325.

(51) Int. Cl.
*A61F 9/007* (2006.01)
*A61B 17/00* (2006.01)
*A61M 5/32* (2006.01)

(52) U.S. Cl.
CPC .... *A61F 9/00763* (2013.01); *A61B 17/00234* (2013.01); *A61F 9/00781* (2013.01);
(Continued)

(58) Field of Classification Search
CPC ............. A61F 9/00763; A61F 9/00781; A61B 17/00234; A61B 2017/00132; A61B 2017/00353
See application file for complete search history.

(56) References Cited

U.S. PATENT DOCUMENTS 5,058,570 A    10/1991    Idemoto et al.
6,217,584 B1    4/2001    Nun
(Continued)

FOREIGN PATENT DOCUMENTS

CN    2130220 Y    4/1993
CN    2149267 Y    12/1993
(Continued)

OTHER PUBLICATIONS

English Language Translation of Korean Office Action of Jan. 19, 2022 in Application KR 10-2019-7012077, cited on Applicant's IDS of Oct. 12, 2022. Translation located on espacenet search of Korean Application documents. (Year: 2019).*
(Continued)

*Primary Examiner* — Ryan J. Severson
*Assistant Examiner* — Cherie M Poland
(74) *Attorney, Agent, or Firm* — Dorsey & Whitney LLP

(57) ABSTRACT

An apparatus for use in tissue removal from a body organ is presented. The apparatus comprises a hand-held probe device, a rotating motor device and a connection assembly configured for removably interconnecting between the hand-held probe device and the rotating motor device. The hand-held probe device is disposable and comprises a housing having proximal and distal ends, a rotatable cutting tool extending distally from the distal end of the housing and being configured for cutting and removing tissue during rotation, and a transmission assembly passing inside the housing between the proximal and distal ends and being
(Continued)

configured for transmitting rotational power to the rotatable cutting tool. The connection assembly is configured for engaging between the rotating motor device and the transmission assembly to thereby controllably rotate the cutting tool and remove tissue. In some embodiments, the apparatus includes a control unit for controlling operation of the apparatus, the control unit comprises an activation mechanism for activating the rotatable cutting tool, and a controller configured for operating the activation mechanism to generate a single fixed activation signal of a known intensity and duration during a predetermined time interval, thereby restricting operation of the cutting tool during the time interval to the single activation signal only.

13 Claims, 8 Drawing Sheets

(52) U.S. Cl.
CPC . *A61M 5/3275* (2013.01); *A61B 2017/00132* (2013.01); *A61B 2017/00353* (2013.01)

(56) References Cited

U.S. PATENT DOCUMENTS

| | | | |
|---|---|---|---|
| 6,328,747 B1 | 12/2001 | Nun | A61B 17/16 604/22 |
| 8,038,692 B2 | 10/2011 | Valencia et al. | |
| 8,181,779 B2 | 5/2012 | Iio et al. | |
| 8,361,098 B2 | 1/2013 | Schachar et al. | |
| 8,500,767 B2 | 8/2013 | Schachar et al. | |
| 9,421,030 B2 | 8/2016 | Cole | A61B 17/32053 |
| 9,421,129 B2 | 8/2016 | Lerner | |
| 2002/0120284 A1 | 8/2002 | Schachar et al. | |
| 2002/0120285 A1 | 8/2002 | Schachar et al. | |
| 2006/0036269 A1 | 2/2006 | Schachar et al. | |
| 2006/0085019 A1 | 4/2006 | Cote | A61B 17/3211 606/167 |
| 2006/0106408 A1* | 5/2006 | Schachar | A61F 2/147 606/166 |
| 2007/0287551 A1 | 12/2007 | Wang et al. | |
| 2008/0172077 A1* | 7/2008 | Valencia | A61F 9/00736 606/170 |
| 2010/0191188 A1* | 7/2010 | Harding | A61M 25/0625 604/164.08 |
| 2011/0160740 A1 | 6/2011 | Makower et al. | |
| 2014/0180321 A1 | 6/2014 | Dias et al. | |
| 2015/0238687 A1 | 8/2015 | Novakovic et al. | |

FOREIGN PATENT DOCUMENTS

| | | | |
|---|---|---|---|
| CN | 1218380 A | 6/1999 | |
| CN | 1355716 A | 6/2002 | |
| CN | 1598345 A | 3/2005 | |
| CN | 201023367 Y | 2/2008 | |
| CN | 101489634 A | 7/2009 | |
| CN | 101507850 A | 8/2009 | |
| CN | 103751889 A | 4/2014 | |
| CN | 105073023 A | 11/2015 | |
| EP | 0709063 A1 | 5/1996 | |
| JP | H0847505 A | 2/1996 | |
| JP | 2004524091 A | 8/2004 | |
| JP | 4970488 B2 | 4/2012 | |
| RU | 2572745 C2 | 1/2016 | |
| WO | WO-0016832 A1 * | 3/2000 | A61M 5/3275 |
| WO | 2013186779 A2 | 12/2013 | |
| WO | 2015145444 A2 | 10/2015 | |

OTHER PUBLICATIONS

Office Action—corresponding Korean Application No. 10-2019-7012077, dated Jan. 19, 2022, 4 pages—English Translation.
Office Action—corresponding Korean Application No. 10-2019-7012077, dated Jan. 19, 2022, 4 pages.
International Search Report for corresponding PCT Application No. PCT/IL2016/051063 mailed Dec. 19, 2016.

* cited by examiner

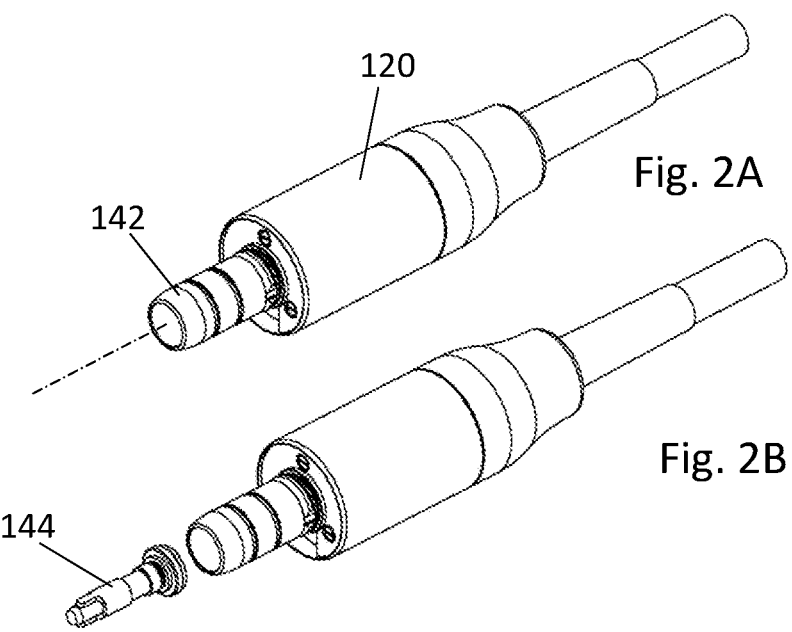
Fig. 2A
Fig. 2B
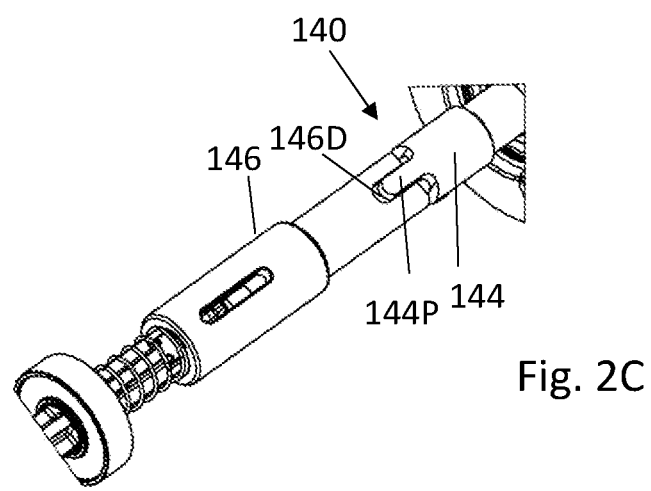
Fig. 2C
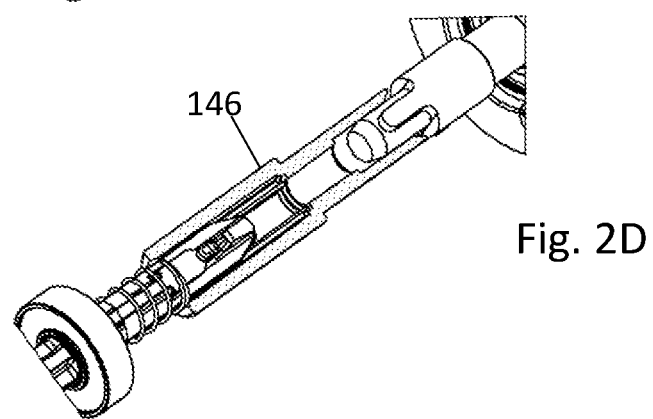
Fig. 2D

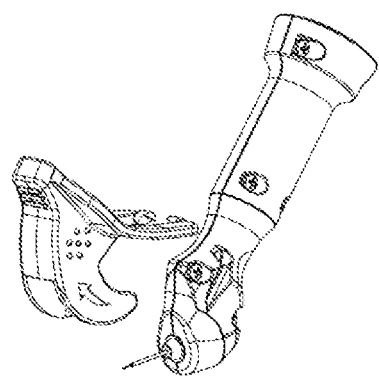
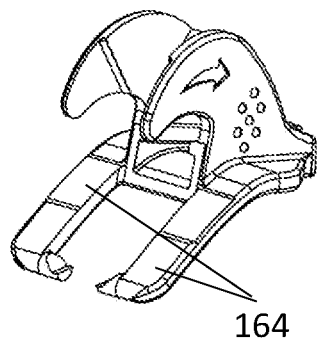
Fig. 3C  Fig. 3D
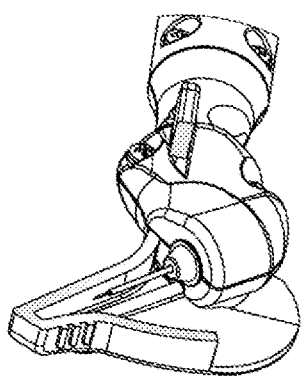
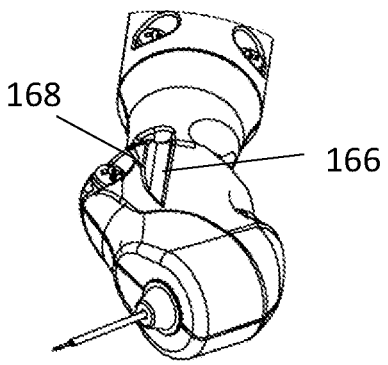
Fig. 3E  Fig. 3F

APPARATUS FOR TISSUE REMOVAL

RELATED APPLICATION

This application is a continuation of U.S. application Ser. No. 16/337,288, filed Mar. 27, 2019, which is a national stage entry of PCT Application No. PCT/M2016/051063, filed Sep. 27, 2016, the entire contents of which are hereby incorporated by reference.

TECHNOLOGICAL FIELD

The present disclosure is in the field of medical devices, and relates in particular to surgical tools.

BACKGROUND

Tissue removal from the body is solicited in various scenarios including for diagnosis or treatment purposes. For example, in biopsy procedure, a sufficiently small tissue specimen is acquired in order to undergo examination outside the body. Usually, the shape of the specimen or the cavity left at the site of the removed tissue have low importance, the body heals from the injury leaving apparently no traces. In another example, cancer treatment may involve tissue removal. Here, it is important to remove as much cancerous tissue as possible. On-line examination is carried to ensure that the ill tissue has been removed. In yet another example, tissue is removed in order to create paths for drainage of excessive liquids such as in Glaucoma condition. In the latter case, full control over the shape and volume of the cavity inside the body is necessary.

In WO2013186779 and WO2015145444, both assigned to the assignee of the present invention and incorporated herein by reference, various embodiments of cutting tools for controllable creation of a channel in the eye wall are described. The cutting tools are directly mounted on a reusable grip unit which includes a rotor to cause rotation of the cutting tool about its longitudinal axis upon actuation of the rotor.

GENERAL DESCRIPTION

The present invention provides a novel full-fledged apparatus for use in controlled tissue removal procedures. The apparatus of the invention is especially useful to use in treating sensitive body organs, such as the eye where accuracy of surgery is a must. The apparatus can then be used to create a diameter-controlled channel in the eye wall to treat glaucoma. The apparatus is user-friendly for both the treating and treated persons. It is safe to use and includes carefully-considered safety measures. Additionally, it assures sterile conditions while keeping the costs reasonable.

The apparatus includes a hand-held disposable probe device which includes a cutting tool, and a separate rotating motor device (a rotor) mounted on the proximal end of the disposable probe. The user grasps the disposable hand-held probe, functioning as a grip unit as well as the cutting tool. By fully separating between the probe and the motor, several advantageous features are gained. First, the probe can be disposable, a one-use only device therefore sterile, made from cost-effective yet durable materials. The rotor can be a multi-use device made from durable materials for long-lasting operation. Second, both the volume and weight of each of the hand-held probe and the rotor are under control to thereby control the overall weight of the device, a crucial factor when it comes to carrying the device by hand in order to perform sensitive and accurate surgical procedures. For example, since the motor is the heavier part, then making it smaller/shorter, by including the necessary transmission assembly within the lighter and disposable probe, keeps the parasite moment forces acting on the whole apparatus (the probe and the motor) balanced, and helps the physician in operating the apparatus by minimizing fatigue. When the lighter disposable probe is longer, the motor rests between the thumb and index fingers, hence increasing the convenience and manageability of the apparatus, whether being used by a right or left hand user.

The connection of the disposable probe to the rotor can be reversible (two opposite orientations), or is possible in a plurality of pivotal orientations between them. This saves effort and time when attaching the rotor to the disposable part, while insures full functionality.

The hand-held probe can be optimized for interaction with the external anatomy (the treated surface) of the body organ, e.g. the eye; its construction has at the top (distal) end a sufficiently short head portion with a preferred inclination angle, relative to the longer handle used to hold the probe. This enables approaching every point in the body organ comfortably from outside. The short head is achieved by positioning the rotor at the back (proximal) end of the hand-held device and providing a suitable transmission assembly from the rotor, through the longitudinal handle, to the cutting tool at the top end.

The apparatus includes a plurality of user-friendly features to maximize its efficiency and ergonomics. The hand-held probe can be used with right and left hands alike. The apparatus includes a backrest for the index finger to enable better grip and control of the cutting tool's orientation. As mentioned above, the positioning of the rotor at the back end of the elongated handle, such that the back end of the handle or the rotor or the interface there between sits between the surgeon's thumb and index finger (on the first dorsal interosseous muscle) functions as a balancing feature (because of the relatively heavier weight of the rotor) and consequently gives the surgeon more accurate control on the three dimensional orientation of the device.

The transmission assembly which passes through the hand-held probe from the rotor to the cutting tool is made from disposable plastic or other low cost and durable material(s). The transmission assembly includes at least two consecutively arranged/coupled parts with at least an inlet part and an outlet part. The outlet part is installed within the hand-held probe's housing in such a way that an axial lash is maintained. Along its operation, the transmission assembly is constructed such that it pushes the cutting tool towards outside the device, i.e. forwardly towards the treated organ, thus enabling better attachment to the organ.

The apparatus applies first-class safety measures both on the mechanical and control aspects. First, it includes a cover that covers the cutting tool before being used. The cover does not open accidentally unless actively opened. It does not open fully unless it passes a certain threshold distance. it opens along a path which does not coincide with cutting tool. It is removable only when fully opened and by pulling it in a different direction than the cutting tool axis and apex. Second, the activation of the cutting tool is controlled and monitored by a dedicated, specifically programmed control unit. The control unit enables to choose predetermined chosen values of the different activation parameters, to suit the specific surgical procedure. In one example, one fixed pulse is generated in response to the activation action; i.e. the output is not direct and continuous, meaning no additional output is generated in response to additional activations during a predefined period of time.

As a flexible solution, the invention can be potentially integrated in treatment machines which are already available in the operating room. For example, a treatment machine provided with a connection to which the hand-held probe and motor devices can be connected, and which can have an upgradable control unit can be used with invention. In this way, the surgeon will be able to perform related treatments from the same machine, while saving treatment time and space in the room.

Thus, according to a first broad aspect of the invention, there is provided an apparatus for use in tissue removal from a body organ, the apparatus comprising a hand-held probe device, a rotating motor device and a connection assembly configured for removably interconnecting between said hand-held probe device and said rotating motor device;

said hand-held probe device being disposable and comprising a housing having proximal and distal ends, a rotatable cutting tool extending distally from said distal end of the housing and being configured for cutting and removing tissue during rotation, and a transmission assembly passing inside said housing between said proximal and distal ends and being configured for transmitting rotational power to said rotatable cutting tool;

said connection assembly being distributed between the proximal end of said hand-held probe device and a distal side of said rotating motor device and configured for engaging between said rotating motor device and said transmission assembly to thereby controllably rotate the cutting tool and remove tissue.

In some embodiments, the apparatus further comprises a control unit configured for connecting to said rotating motor device and being configured and operable to activate the rotating motor device in a controlled activation mechanism.

In some embodiments, the connection assembly is configured to enable connecting said rotating motor device to said hand-held probe device in at least two relative orientations. In yet some embodiments, the connection assembly comprises a reversible connector.

In some embodiments, said housing comprises an elongated body and a head body successively arranged from said proximal end to said distal end of the housing. Said elongated body and head body can be formed as an integral member. Said head body can be oriented with a predetermined angle with respect to the elongated body, said predetermined angle being selected in accordance with an orientation of a treatment surface of the body organ. Said elongated body can have a predetermined length selected to provide a stable holding position of the apparatus during operation. Said stable holding position can be such that said rotating motor device rests on first dorsal interosseous muscle of a user holding the apparatus.

In some embodiments, said hand-held probe comprises a holding portion enabling a user to control three-dimensional orientation of the rotatable cutting tool. Said holding portion can comprise a depression in which a user positions his index finger, to thereby control the three-dimensional orientation of the rotatable cutting tool. Additionally or alternatively, said holding portion can be configured for enabling left- or right-hand user to operate the apparatus.

In some embodiments, said transmission assembly exerts both rotational and forward forces on the cutting tool, thereby enhancing attachment of the cutting tool to the body organ during operation.

In some embodiments, said housing comprises a removable cover configured to safely cover the cutting tool when not in use. Said cover can be configured to move in a predefined spatial path between a closed state covering said cutting tool and an open state revealing said cutting tool, while still being attached to the housing. Said hand-held probe can comprise a safety opening mechanism configured to return said cover to its closed state if the cover does not pass a predetermined distance along said spatial path. Additionally or alternatively, said hand-held probe can comprise a safety locking mechanism configured to keep said cover in said closed state unless pushed by the user along said spatial path. Said cover can be configured to be removable from said housing only when in its open state. Said open state of said cover can be configured to enable removing the cover by pulling it in a direction different from the cutting tool's longitudinal axis.

In some embodiments, said control unit comprises a touch screen.

In some embodiments, said control unit is preprogrammed to activate said rotating motor by generating a single fixed activation signal of a known rotation speed and duration during a predetermined time interval.

In some embodiments, the apparatus further comprises a pedal for activating predetermined activation functions, to controllably rotate said cutting tool.

In some embodiments, said body organ is the eye, said cutting tool being configured to form a channel in the sclera.

According to another broad aspect of the invention, there is provided a control unit for controlling operation of a tissue removal apparatus for tissue removal from a body organ, the control unit comprising an activation mechanism for activating a cutting tool of the tissue removal apparatus, and a controller configured for operating said activation mechanism to generate a single fixed activation signal of a known intensity and duration during a predetermined time interval, thereby restricting operation of the cutting tool during said time interval to said single activation signal only.

According to yet another broad aspect of the invention, there is provided a hand-held probe device comprising a rotatable cutting tool and being configured for connecting said cutting tool to an external rotating motor device, thereby enabling said probe device with the cutting tool to be disposable; said hand-held probe device comprising: a hollow housing having proximal and distal ends and comprising an elongated body and a head body successively arranged with a predetermined angle therebetween from said proximal end to said distal end; and a transmission assembly passing inside said housing and being connected at one end to said cutting tool and at the other end to a connection assembly associated with said rotating motor device to thereby controllably transfer power from the rotating motor device to the cutting tool.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 2A-2E illustrate a non-limiting example of a connection assembly for connecting between a hand-held probe and a rotating motor configured in accordance with the present invention;

FIGS. 3A-3F exemplify a safety cover and variety of safety mechanisms included in the hand-held probe of the present invention;

DETAILED DESCRIPTION OF EMBODIMENTS

Figure 1A:
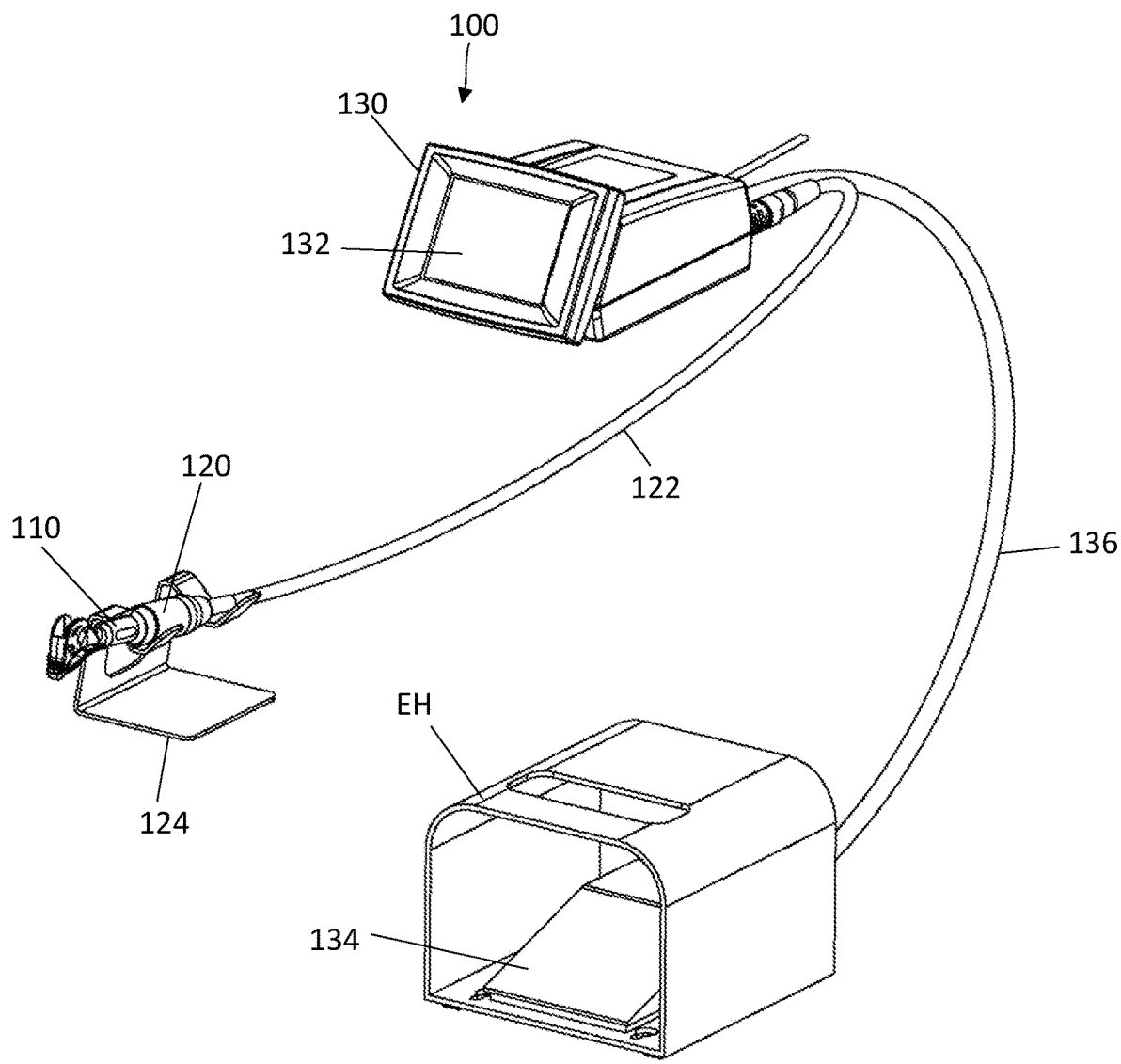
FIGS. 1A-1D illustrate a non-limiting example of an apparatus configured in accordance with the present invention.
Figure 1B:
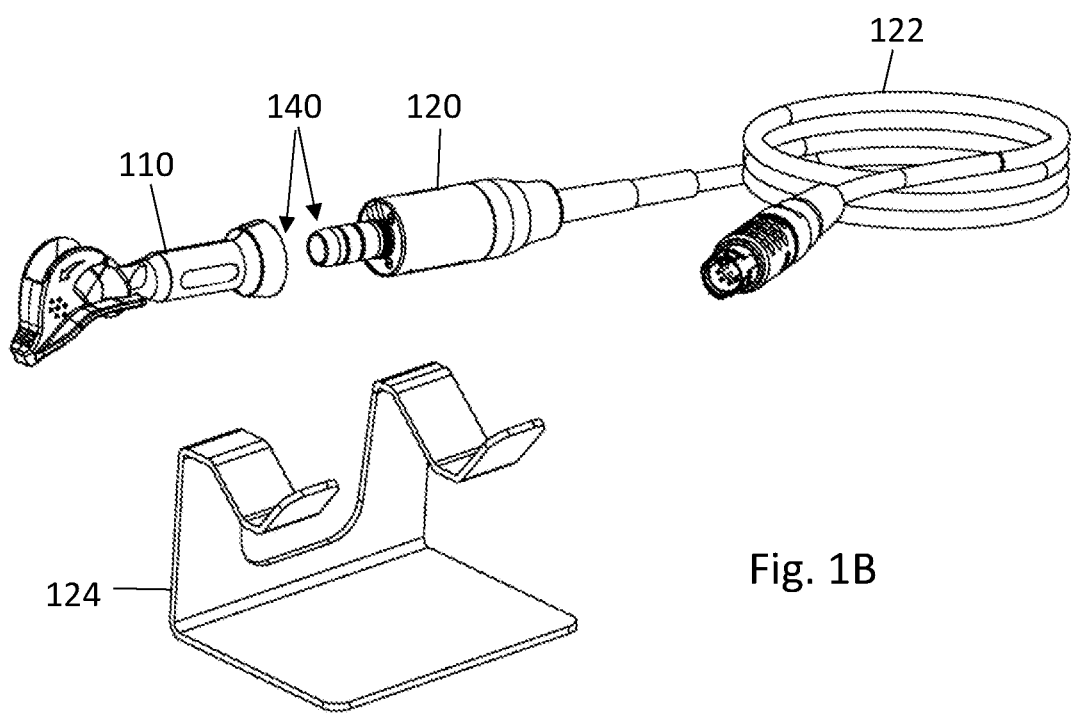

Reference is made to FIGS. 1A-1D illustrating a non-limiting example of a medical apparatus 100 configured according to the present invention. The medical apparatus 100 is configured for use in procedures involving tissue removal from a body organ, e.g. removing tissue from an eye such as to create a channel in the sclera tissue of the eye to allow draining of extra fluid accumulating inside the eye, a symptom that causes various medical conditions and/or complications. As shown in FIG. 1A, the apparatus 100 includes a hand-held probe device 110 which includes a rotatable cutting/surgical tool that cuts and removes the tissue, and a rotating motor device 120 that causes rotational movement of the cutting tool to remove the tissue. the hand-held probe and the rotating motor device, being enclosed in separate housings, are interconnected by a connection assembly 140, as briefly shown in FIG. 1B and as will be described further in detail below with reference to FIGS. 2A-2E. The apparatus 100 can also include, as shown, a control unit 130 that controls the operation of the rotating motor device and the cutting tool. Also shown in the figures, an optional stand 124 configured to safely hold the hand-held probe device when not being in use, and an optional pedal 134 by which a user can activate the control unit and/or the rotating motor.

Figure 1C:
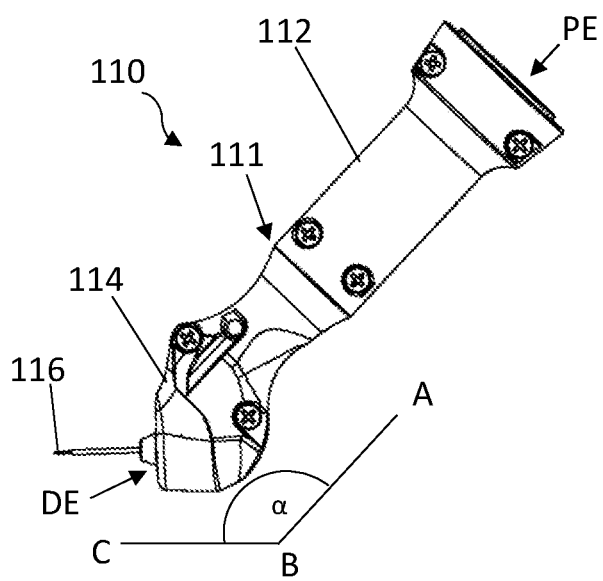

As shown in FIG. 1C, the hand-held probe 110 includes, on the outside, a housing 111 extending between a proximal end PE and a distal end DE, and a rotatable cutting tool 116 extending distally from the distal end of the housing. In this application the word "distal" indicates the patient side, while the word "proximal" indicates the operator/physician side. The rotatable cutting tool 116 is configured for cutting and removing tissue during rotation. The cutting tool 116 can be configured as described in WO2013186779 titled "Medical Device, Assembly and Method for Creating a Channel in Soft Tissue" and in WO2015145444 titled "Medical Device for Tissue Removal", both assigned to the assignee of the present invention and are incorporated herein by reference. On the inside, the housing of the hand-held probe encloses therein a transmission assembly configured to transmit rotational power from the rotating motor device 120 to the cutting tool 116 to thereby cause its rotation. An example of a transmission assembly is described herein below with reference to FIG. 1D.

The housing of the hand-held probe device can be formed as an integral member having a unibody configuration or it can be formed from more than one part, e.g. two parts. In either case, the housing can have more than one longitudinal axis along its length, between the proximal and distal ends. Having a plurality of longitudinal axes can be useful in that it enhances flexibility and access of the rotatable cutting tool to the treated organ in the three dimensional space. By tilting the housing at at-least one point along its length or by including two or more successive parts inclined by predetermined angles there between, with respect to each other, the three dimensional orientation of the probe as well as the cutting tool with respect to a treatment surface, being the organ's surface faced by the cutting tool, can be controlled.

In the described example, as shown in FIG. 1C, the housing includes an elongated body 112 at a proximal side (i.e. at the side of the user, far from the patient) and a head body 114, on which the rotatable cutting tool 116 is mounted, at a distal side (at the side of the patient, far from the user). As can be seen, the head 114 is oriented with a predetermined angle α with respect to the elongated body 112. The predetermined angle α can be defined in several ways. In the example shown, it is defined as the angle between the longitudinal axes of the elongated body 112 and the cutting tool 116, where the angle's rays AB and BC are parallel to the longitudinal axis of the elongated body and to the longitudinal axis of the cutting tool, respectively. The predetermined angle α is chosen based on the specific medical application to enable effective and comfortable access to the tissue removal site, in other words it is chosen to provide better or optimal ergonomics for holding the device with respect to the tissue treatment site. Consequently, the predetermined angle is selected to enable access of the cutting tool 116 to every point on the body organ, taking into account the curviness of the organ/treatment surface, while the user holds the probe 110 with his hand. The predetermined angle α is determined based on several factors, including, inter alia, absolute lengths of the elongated body and the head, or the relative length between them; length of the cutting tool; anatomy of the treated organ and its surrounding. The value of a is typically equal to or larger than 90° up to a maximum of 180°. In the case of treating the eye, a is chosen to be close or equal to 135°.

The apparatus of the present invention increases the safety of the patient and minimizes any risk of infection. According to preferable embodiments, the whole hand-held probe 110 is disposable, such that it is used once and on one patient at a time. As such, the whole probe 110 is made from materials that enable its disposal, such as different medical grade polymers, e.g. biocompatible polymers, with the exception of the cutting tool being made from biocompatible metal, ceramic or the like. At the same time, as the probe is used for short time, it can be made from affordable yet durable materials. For example, the probe housing can be made from Polycarbonate (plastic parts), and the surgical tool from Corrosion Resistance Steel (CRES) 420F.

Figure 1D:
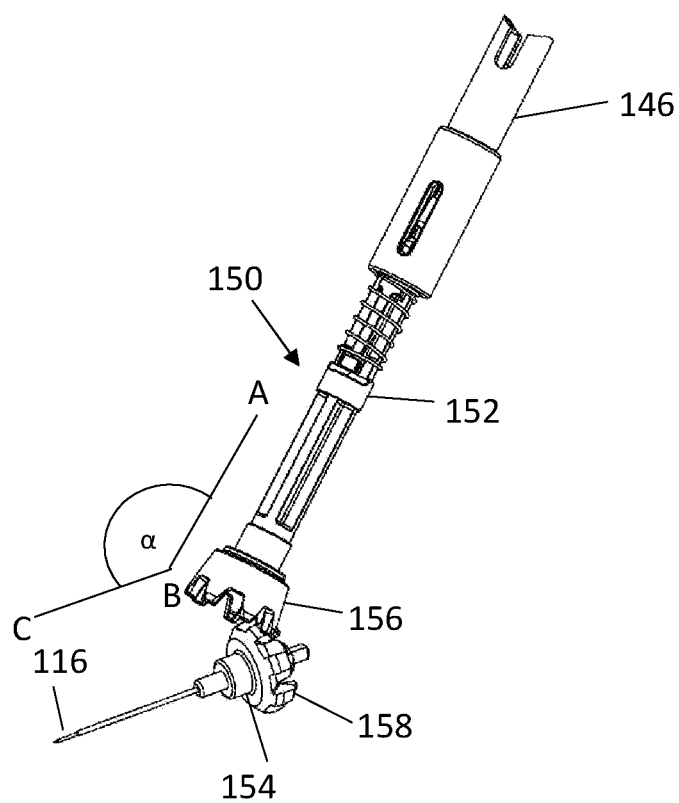

FIG. 1D illustrates a non-limiting example of a transmission assembly 150 configured according to the invention. The transmission assembly which is accommodated inside the housing 111, e.g. the elongated body 112 and the head body 114, is made from light-weight and disposable, yet durable materials, such as polymers. The transmission assembly is designed and selected to withstand rotational speed of tens of thousands of rpm. In specific situations, as when removing soft tissue as the sclera in the eye, the speed is chosen to be around 8,000 rpm, which is sufficient but not oversized. Further, the transmission assembly enables effective transmission of the rotational power and includes minimum number of separate elements to achieve this. In the described example, the transmission assembly 150 includes three parts: a clutch 146, an inlet shaft 152 coupled to the clutch and an outlet shaft 154 coupled to the inlet shaft. The distal portion of the inlet shaft 152 includes an inlet gear 156 which is coupled to an outlet gear 158 formed at the proximal portion of the outlet shaft. The transmission assembly exerts both rotational and forward forces on the cutting tool 116, thus enhancing attachment of the head body, and the cutting tool, to the body organ during treatment. In the example shown, the outlet shaft 154 has certain axial lash, and the gear profile creates a force vector directed forwardly to the distal direction. After attaching the motor device to the probe device, the clutch and inlet shaft are fixedly attached as a single rigid element and turn together as one part during rotational movement.

The rotating motor 120 connects, by its distal side, to the proximal end (PE in FIG. 1C) of the probe 110, via the connection assembly 140 which is located at the proximal end of the probe and the distal end of the rotating motor, to thereby cause rotation of the cutting tool 116 via the transmission assembly passing inside the probe's housing. The rotating motor can include an integrated sensor such as a magnetic, optical or other kind of encoder. In the case of a magnetic encoder, the configuration may be such that the encoder has a magnet with numerous polarities connected to the rotor part of the motor. Reading of the magnet polarities change is done by dedicated sensors, e.g. HOLE sensors, which are static and assembled inside the housing of the rotating motor. The sensor can be responsible for motor speed detection, rotation direction detection and number of rounds calculation. The motor type can be a brush or brushless motor or any other suitable kind.

The control unit 130 controls the operation of the motor 120 via a connection 122, which in the shown example is a wired connection. In some embodiments, the connection can be wireless. As will be further detailed below, the control unit 130 activates the motor 120 and causes the rotation of the cutting tool 116 in response to a function selection made by the user via a control panel 132 on the control unit 130. In some embodiments, as will be further described below, the control panel 132 includes a touch screen to select activation functions and/or parameters.

In some embodiments, such as in the example shown, the apparatus 100 further includes a pedal 134 which the user presses down by his foot to activate the rotating motor, based on a function preselected on the control unit 130. Similarly, the pedal is connected to the control unit via a connection 136, which in this example is a wired connection, however a wireless connection can be equally used. The pedal can be positioned inside an enclosing housing EH that minimizes accidental foot-pressing. It is only when the user inserts his foot inside the enclosing housing that he can press the pedal. As a result, unintentional pressing and activation of the rotating cutting tool is avoided. In addition, the enclosing housing functions as a guide for the operator. When the operator is focused on the patient and microscope he is able to find the pedal enclosure and to navigate his foot directly inside without the help of others.

The apparatus of the invention enables independent and fully-functional usage by the physician alone. Using a pedal enhances this by allowing the physician to independently use the apparatus by holding the probe in one hand and keeping the other hand free which he can then use to hold the patient or to hold another accessory/device needed in the process.

Figure 2E:
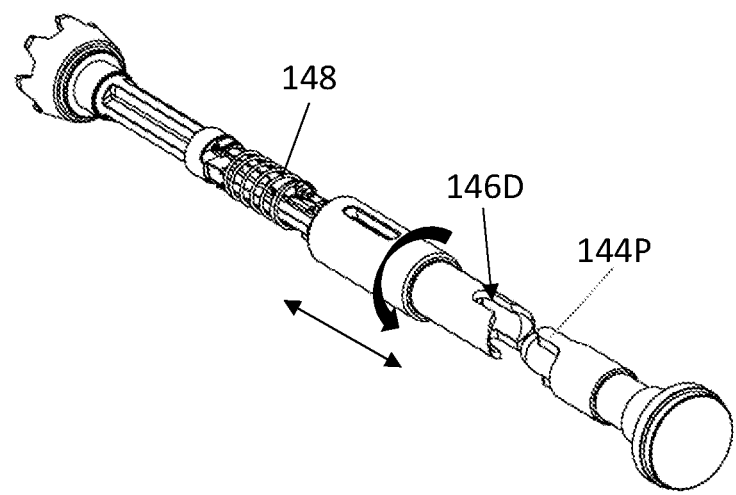

Reference is made to FIGS. 2A-2E illustrating a non-limiting example of a connection assembly 140 configured according to the present invention. according to the invention, the connection assembly allows connecting the rotating motor 120 to the probe 110 in at least two orientations, relative to each other. The connection assembly is typically distributed between the hand-held probe, at its proximal end, and the rotating motor, at its distal side. In the described example, the connection assembly 140 provides a reversible connection between the motor and the probe, i.e. it allows connection between both devices in two opposite (180°) orientations. As shown in FIGS. 2A and 2B, the motor 120 has at its distal side, the side connecting to the probe, one of the two elements of the connection assembly, where a hollow rod 142 extends distally and in which a rotatable shaft 144 is installed. An exploded view is shown in FIG. 2B. The rotatable shaft 144 connects at its proximal end to the rotating motor 120 so as to transmit the rotational movement down the way to the cutting tool 116. The probe 110 includes at its proximal side the clutch 146 forming the second element of the connection assembly 140. As can be seen in FIG. 2C the clutch 146 and the rotatable shaft 144 engage together in a male-female engagement mechanism, such that two protrusions 144P on the shaft 144 engage with two corresponding depressions 146D formed in the proximal end of the clutch 146. The engagement between the protrusions and the depressions is further illustrated in FIG. 2D which shows a longitudinal cross-sectional view of the clutch 146.

As shown, the two protrusions 144P, as well as the two depressions 146D, are identical and formed in a 180° with respect to each other. As a result, the connection is reversible and the probe and the motor are connectable to each other even if one is turned with a 180° with respect to the other during the engagement process. It is noted that the protrusions and the corresponding depressions may be more than two, and in such a case they can be equally spaced from each other along the perimeter of the base of the clutch 146 and the shaft 144.

According to one aspect, the connection assembly enables effortless and seamless attachment between the probe and the motor, such that the user does not need to turn either in order to align them or look at the end sides of the probe and motor when he/she attaches them. In some embodiments, the connection assembly includes axial or rotational movement of one of the two engaging elements with respect to the other. In the described example, as shown in FIG. 2E, the clutch 146 is freely movable with respect to the probe 110 both axially and azimuthally. This helps in the attachment process and makes it seamless and unsupervised, because even if the protrusions and depressions are not aligned, when the probe and motor are brought together, then when the user pushes the rotatable shaft against the clutch in the distal direction, a spring 148 pushes the clutch in the opposite proximal direction thus causing the clutch to rotate until the protrusions align with the depressions and the engagement is achieved. The engagement between the motor device and the hand-held probe device involves their internal rotating parts, i.e. the rotatable shaft 144 at the motor side and the inlet shaft 152 at the disposable probe side, which start to move together either in 1:1 transmission ratio or in other predefined ratio. The latter case is particularly useful in case the motor is designed to work in a constant speed while it allows different output speeds for the transmission assembly and the cutting tool. While the internal rotating parts engage as described, the outer housings of the motor device and the hand-held disposable device are not necessarily engaged. In one specific case, they are free to turn with respect to each other. This feature enhances the manageability of the probe by the user as it prevents or at least minimizes parasite moments which might be caused by the wired connection 122 when the probe and motor devices are moved by the user.

Reference is made to FIGS. 3A-3F illustrating a non-limiting example of a cover used with the disposable probe to keep the cutting tool safely covered when not in use, so to prevent accidental injury. According to the invention, the cover is configured to move in a predefined spatial path between a closed state covering the cutting tool and an open state revealing the cutting tool while still being attached to the head body of the probe. The cover enhances the safety further as it needs to pass a threshold distance along the spatial path in order to finally stay open, otherwise it returns back autonomously to its closed state. Additional safety measure is guaranteed since the cover does not detach from the probe unless it is in its open state, therefore accidental encounter with the cutting tool is prevented or at least minimized, inter alia because the direction of detachment is different from the axis of cutting tool, such that even during an unsuccessful removal of the cover, the user's hand does not accidentally move towards the cutting tool or at least its sharp apex. Yet further, additional safety is guaranteed by a safety locking mechanism which keeps the closed cover in place as long as no force is applied on it in order to open it.

Figures 3A, 3B:
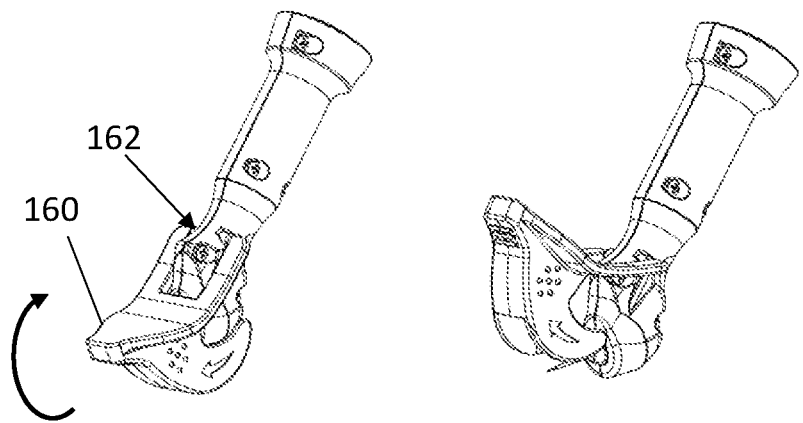

In the described example, as shown in FIGS. 3A and 3B, the cover 160 moves in a curved path, e.g. circular or semi-circular, around a hinge point 162 formed by a dent in the probe's housing, e.g. in the head body, to reveal the cutting tool. The cover 160 moves upwards, and not downwards, to facilitate its removal by the user. When the cover's front reaches a certain position, it can be pulled off the probe. If the cover does not pass a predetermined distance towards its open state, it returns back to its closed state, such that it cannot be kept in a partially opened state in which the risk for accidental injury increases. The threshold safety mechanism can be implemented in different ways, such as by providing a spring that acts against the movement until it loses its elasticity, or until the cover is locked at its open state by a suitable protrusion that prevent its back movement. In the described example, the threshold safety is achieved by the special structure of the side bars which act like springs, pushing the cover 160 towards the front of the probe if the cover does not reach the open state and get locked therein.

In addition, the probe includes a locking safety mechanism which keeps the cover closed and prevents its accidental opening. Such a safety mechanism is achieved in the described example by providing a depression 166 in the probe's housing, such as a dent in the head body, which traps the side bars 164 and keeps them in a closed state, as shown in FIGS. 3E and 3F. Opening the cover requires overcoming a protrusion 168 such that the side bars spread to climb over the protrusions 168 on both sides.

In addition to the above-mentioned safety mechanisms, the apparatus includes an electrical safety mechanism. The control unit activates the rotating cutting tool after receiving an input of a predetermined duration from the user. The input from the user can be provided via the control panel, e.g. by pressing an icon, or the provided pedal, for a predetermined duration. For example, when a pedal is provided, if the user presses the pedal for a period shorter than a predetermined period (e.g. half a second), the control unit does not activate the cutting tool. This helps in minimizing unintentional activation of the cutting tool.

Figure 4A:
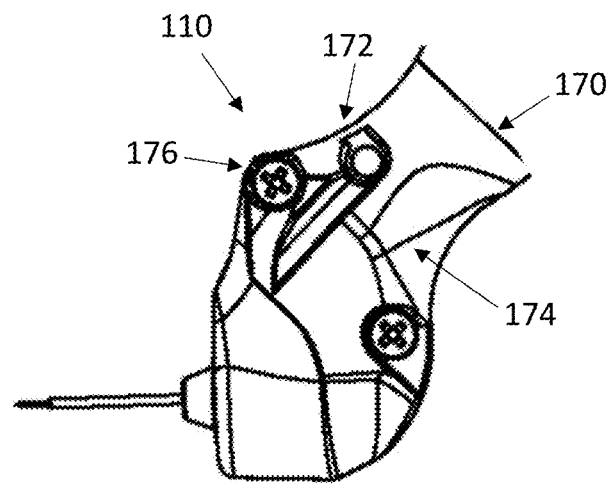
FIGS. 4A-4B illustrate various functional features included in the hand-held probe of the present invention.
Figure 4B:
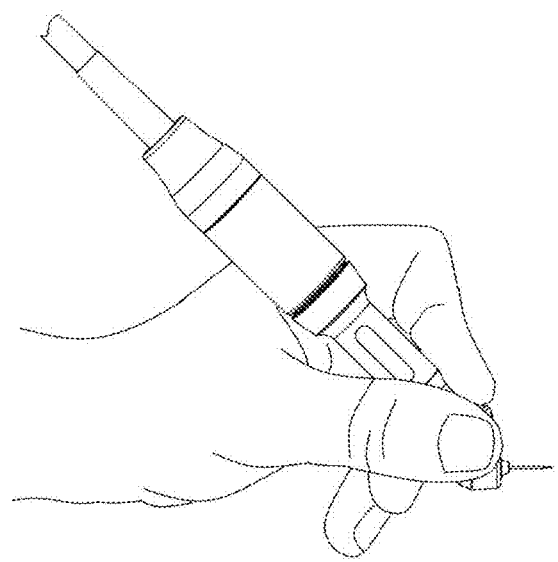

The present invention enhances the ergonomics of the probe to enable convenient, effective and controlled usage. Such requirements are especially important when treating sensitive organs such as the eye, because precise orientation of the probe and control over the power exerted by the operator are important. Reference is made to FIGS. 4A-4B illustrating non-limiting examples of ergonomics enhancing features. In some embodiments, as shown in FIG. 4A, the probe 110 includes an ergonomic holding portion 170 at its distal side, which is aimed at facilitating the probe's grasping. The holding portion includes dedicated depressions 172 and 174 for positioning the index finger and the thumb respectively. The holding portion also includes a protrusion 176, in the vicinity of the depression 172, which acts as a pointer when the user pushes his index finger against it. In addition, the probe of the invention, e.g. its holding portion, is configured to be ambidextrous, equally used by both right and left handed users. FIG. 4A shows a right hand holding the probe and FIG. 4B shows a left hand holding the probe.

Figure 5:
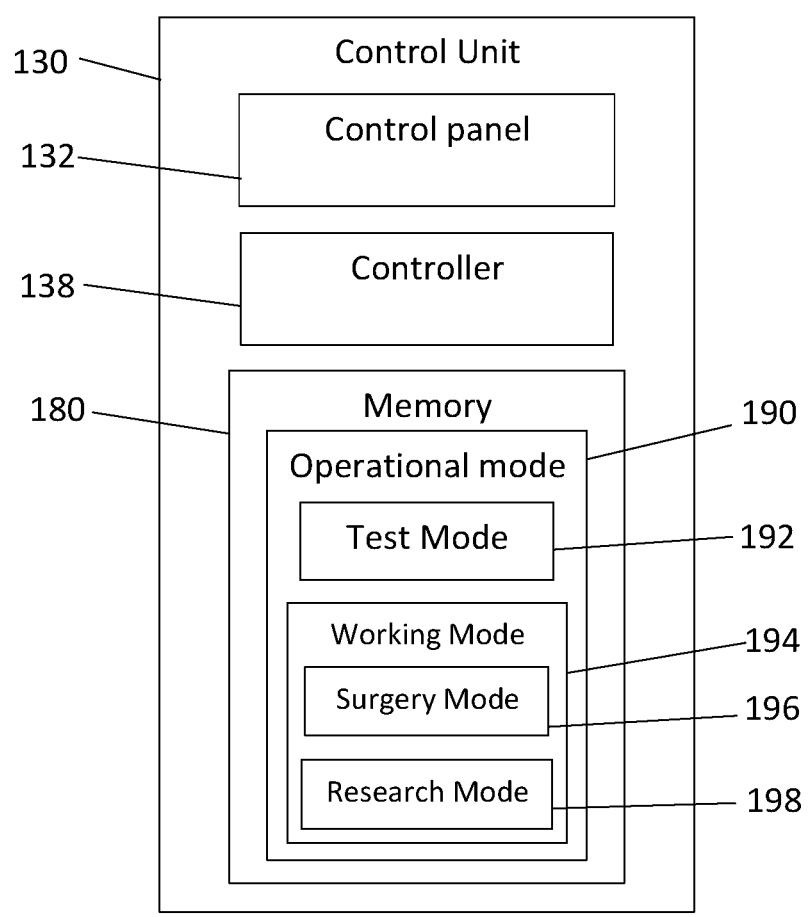
FIG. 5 exemplifies various components of the control unit of the present invention.

Reference is made to FIG. 5 illustrating non-limiting examples of the control unit of the apparatus with the included control panel which can be in the form of a touch screen configured to enable controlling the operation of the apparatus. The control unit is a computing device that controls the operational mode of the apparatus including treatment parameters or functions of the surgical process as well as a test process. In the figure, a schematic illustration of the components of the control unit 130 is shown. The control unit 130 includes the control panel 132 which is configured to enable the user to select a desired operational mode 190 saved in a memory 180. A controller 138 configured to execute the chosen operational mode, including parameters or functions, is included in the control unit and connected to the memory 180.

The operational modes 190 include a test mode 192 and a working mode 194, the latter includes a surgery working mode 196 and a research working mode 198.

The control unit 130, utilizing the controller 138, continuously monitors the operation of the apparatus parts to insure normal operation of the apparatus. For example, the following are monitored: connection between the different parts (the motor and probe, the motor and control unit, the control unit and foot switch (pedal)), the speed of the motor, the time of pressing the pedal by the user, number of motor activations as an indicator for motor life time (e.g. 250 cycles) which is limited due to sterilization load. The apparatus can include suitable sensors (not shown) which deliver information to the controller 138 about the operation of the apparatus and its different parts, including the monitored parameters described above. One example is the magnetic encoder described above with respect to the rotating motor device. In some examples, the controller sends signals (e.g. electrical) to the motor device and/or to the pedal device every certain predefined time interval (e.g. every 100 milliseconds) and based on the signal received a fault can be detected and a suitable alert output is generated. The controller 138 may include a programmable chip enabling to add or modify features of the controller.

The test mode 192 can be a self-test mode which runs automatically each time the apparatus is turned on or each time an operational fault is detected by the monitoring controller, such as a fault in the connection between the control unit and the motor. Additionally or alternatively, the test mode 192 can run upon user's request by selecting it via the control panel 132. The controller 138 outputs a suitable alert according to the error found during the running of the self-test or according to the continuous monitoring applied during the working modes 194 as described above. In one example, the test mode examines the speed of the motor in order to detect failures or alert about end of life. In such case, the controller activates the motor for a predetermined time period and counts the number of rounds the motor performed and compares the result to a value saved in the memory 180. If the result is out of a predefined range around the saved value, the controller generates a fault alert. The alert may, for example, indicate that the motor may have completed its life cycle and needs to be replaced, that the cable connector is not working as specified or that the sensor monitoring the motor is not working as specified.

Upon finishing the test mode, the controller 138 can be programmed to automatically move the apparatus to the working mode 194. By default, the surgery working mode 196 is selected. This mode is a predefined mode which has the operational parameters of the apparatus fixed at predetermined recommended values that suit the specific surgical operation, the body organ specifications, the treated population/race or the treated species. The control unit can be programmed to include a plurality of surgery working modes, each with saved predefined operational parameters, which the operator can access by a mere press of a button on the control panel (e.g. an icon/tile on a touch screen). For example, when removing tissue from the sclera tissue in the eye, the motor speed is determined to be 8000 RPM and the time for each activation is determined to be 0.4 sec. However, when treating animals, e.g. horses or dogs who suffer from excessive pressure in their eyes, the values are different and specific to the treated species. The saved values of the operational parameters can be recommended values chosen based on experience and/or experiments.

If exploring a new surgical operation or a new body organ/tissue, the apparatus can be put into a research working mode, which enables the user to control and change the parameters values. To assure safe usage, accessing the research working mode can be protected with a pin or password. The parameters which can be controlled include, inter alia, the speed of rotation, the duration of rotation, the direction of rotation (clockwise, counter clockwise, or a combination thereof) and the transmission ratio between the motor and the cutting tool. The user can then save a new working mode including the values of the parameters that he used in the research to be easily accessed again in the future.

The control panel includes a friendly user-interface that allows the user to choose the operational mode of the device as well as the different operational parameters.

Thus, the present invention provides an apparatus that enables a comprehensive, powerful and safe solution for tissue removal from the body. In addition, as described above, the invention may be powerfully integrated within other treatment apparatuses, thereby saving place and complexity inside the operating rooms.

The invention claimed is:

1. A hand-held probe device, comprising:
 a housing having proximal and distal ends, the proximal end being configured for connecting the hand-held probe device to an external motor device,
 a cutting tool extending distally from said distal end of the housing and being configured for cutting and removing tissue when activated by said external motor device, and
 a removable cover configured to be attached to the housing at the distal end, to safely cover the cutting tool when the device is not in use and to be removed from the housing prior to activating the cutting tool, the cover being connectable via a hinge to the housing and configured to move in a predefined curved path, around the hinge, between a closed state totally covering said cutting tool and a fully open state revealing said cutting tool, while still being attached to the housing, the attached cover detachable from the housing only when in the open state and in a detachment direction different from an axis or apex of the cutting tool.

2. The probe device according to claim 1, comprising a safety locking mechanism configured to keep said cover in said closed state unless pushed by a user along said curved path.

3. The probe device according to claim 1, comprising a safety opening mechanism configured to return said cover to its closed state, when a user attempts to open the cover, if the cover does not pass a predetermined threshold distance along said curved path, such that the cover cannot be kept in a partially opened state.

4. The probe device according to claim 1, wherein said hinge is formed by a dent in the housing.

5. The probe device according to claim 1, wherein said housing comprises a holding portion enabling ergonomic holding and three-dimensional orientation control of the probe device, the holding portion including dedicated depressions for positioning the index and thumb fingers of a user.

6. The probe device according to claim 5, wherein said holding portion is shaped for enabling left- or right-hand user to operate the apparatus.

7. The probe device according to claim 1, wherein said housing comprises an elongated body and a head body successively arranged from said proximal end to said distal end of the housing.

8. The probe device according to claim 7, wherein said head body is oriented with a predetermined angle with respect to the elongated body, said predetermined angle being selected in accordance with an orientation of a treatment surface of a body organ.

9. The probe device according to claim 1, comprising a transmission assembly passing inside said housing, between said proximal and distal ends, and being configured for transmitting power from the external motor device to said cutting tool.

10. The probe device according to claim 9, wherein said transmission assembly is configured to transmit rotational power from the external motor device to the cutting tool, and to exert a forward force on the cutting tool thereby enhancing attachment of the cutting tool to a treated body organ during operation.

11. The probe device according to claim 9, wherein said transmission assembly is made from polycarbonate or polymer materials.

12. The probe device according to claim 1, comprising a connection assembly at the proximal end of the housing being configured for connecting the probe device to the external motor device while avoiding a need for alignment of the probe device with respect to the external motor device to enable the connection.

13. The probe device according to claim 1, being disposable, said housing and cover being made from polycarbonate or polymer materials.

* * * * *